United States Patent [19]

McCaulay et al.

[11] 4,214,116
[45] Jul. 22, 1980

[54] HYDROCARBON ISOMERIZATION UTILIZING A HYDROCARBON PROMOTER WITH TANTALUM PENTAFLUORIDE AND HYDROGEN HALIDE CATALYST

[75] Inventors: David A. McCaulay, Homewood; Thomas D. Nevitt, Naperville, both of Ill.

[73] Assignee: Standard Oil Co. (Indiana), Chicago, Ill.

[21] Appl. No.: 47,060

[22] Filed: Jun. 11, 1979

[51] Int. Cl.$^2$ .............................................. C07C 5/28
[52] U.S. Cl. ..................................................... 585/747
[58] Field of Search ......................................... 585/747

[56] References Cited

U.S. PATENT DOCUMENTS

| | | | |
|---|---|---|---|
| 4,048,251 | 9/1977 | Cahn et al. | 585/747 |
| 4,058,575 | 11/1977 | Cahn et al. | 585/747 |
| 4,065,381 | 12/1977 | Say et al. | 585/747 |
| 4,065,405 | 12/1977 | Hulme | 585/747 |
| 4,069,268 | 1/1978 | Siskin et al. | 585/747 |
| 4,105,704 | 8/1978 | Say et al. | 585/747 |

*Primary Examiner*—George Crasanakis
*Attorney, Agent, or Firm*—James R. Henes; William T. McClain; William H. Magidson

[57] ABSTRACT

An isomerization process which comprises isomerizing a hydrocarbon component comprising at least one saturated $C_5$–$C_6$ hydrocarbon in the presence of hydrogen and a catalyst comprising tantalum pentafluoride and hydrogen halide and in the presence of a hydrocarbon promoter comprising at least one member selected from the group consisting of $C_8$–$C_{14}$ multiple-branched paraffins, wherein the total concentration of $C_8$–$C_{14}$ multiple-branched paraffins, is in the range of about 1 to 50 parts by weight per each 100 parts by weight of said saturated $C_5$–$C_6$ hydrocarbons.

9 Claims, No Drawings

HYDROCARBON ISOMERIZATION UTILIZING A HYDROCARBON PROMOTER WITH TANTALUM PENTAFLUORIDE AND HYDROGEN HALIDE CATALYST

This invention relates to a process for isomerization of feedstocks comprising $C_5$ and/or $C_6$ saturated hydrocarbons. More particularly, this invention relates to improved isomerization of light-naphtha streams containing such hydrocarbons, for use in blending gasoline.

In the petroleum refining industry the demand for high octane gasoline has increased development of isomerization, alkylation, and other upgrading treatments for hydrocarbon feedstocks. The use of metal pentafluorides such as tantalum, niobium, and antimony pentafluorides in halogen acid solvents for acid catalyzed reactions has been described. For example, U.S. Pat. No. 2,683,764 (Lien et al, 1954) discloses that HF-$TaF_5$ is a powerful catalyst for isomerization, alkylation, cracking and other reactions, and U.S. Pat. No. 3,948,761 (Siskin et al, 1976) discloses that HF-$TaF_5$ is a preferred catalyst system for the isomerization of acyclic and alicyclic aliphatic hydrocarbons.

Hydrogen is typically employed in paraffin isomerization in order to inhibit cracking and the advantage of tantalum pentafluoride catalyst over pentafluorides of antimony or niobium is that tantalum is not reduced in hydrogen, whereas antimony and niobium are reduced from the active $+5$ to the inactive $+3$ valence state.

U.S. Pat. No. 4,064,189 (Siskin et al, 1977) which is incorporated herein by reference, discloses the preparation of high octane alkylates by selectively alkylating paraffinic hydrocarbons with other paraffinic hydrocarbons at alkylation conditions in the presence of hydrogen and of a catalyst comprising a metal pentafluoride selected from the group consisting of tantalum pentafluoride, niobium pentafluoride and mixtures thereof and a hydrogen halide, to produce a mixture containing primarily $C_4$–$C_6$ isomerized paraffins. Siskin et al disclose "The present catalyst system is particularly suited for use in refinery alkylation processes. The process of this invention contemplates the use of various refinery streams as feedstock. For example, the smaller paraffin can be obtained from $C_5$–$C_6$ light virgin naphtha, while the larger paraffin can be obtained from virgin naphtha reformer feeds, cat naphtha raffinate, Fisher Tropsch products, etc." (column 5, lines 53–60). In broadly describing feedstocks for their process, the patentees disclose in column 4:

Paraffinic hydrocarbon feedstocks that are suitable for use in the present invention include the aliphatic and cycloaliphatic hydrocarbons. The aliphatic hydrocarbons (straight and branched chain materials) contain 3 to 12 carbon atoms per molecule ($C_3$–$C_{12}$), preferably 4–12 carbon atoms ($C_4$–$C_{12}$), and may be exemplified by propane, n-butane, isobutane, pentanes, hexanes, heptanes, and the like. The cycloaliphatic hydrocarbons (naphthenes) contain 5 to 15 carbon atoms per molecule, particularly 6 to 12 carbon atoms, and may be exemplified by methylcyclopentane, dimethylcyclopentane, ethylcyclohexane, n-pentylcyclohexane and the like.

All of the examples presented by the patentees employ straight-chain paraffins of six or more carbon atoms for the larger paraffin alkylation feed as generally represented by Example 3 in which a mixture of normal heptane, normal octane, normal nonane, normal decane, and normal undecane was reacted with isobutane in the presence of $TaF_5$ catalyst. In Example 4, the patentees reacted a mixture of normal paraffins and cycloparaffins with isobutane in the same catalyst system to demonstrate simultaneous isomerization and alkylation.

Siskin et al further contemplate that diisobutylene and triisobutylene polymers, codimers of normal butylenes and the like can be broken down into smaller units and alkylated according to their process, as disclosed in column 4, lines 27–35. However, these olefinic materials can form polyunsaturated "red-oil" which can complex with and deactivate $TaF_5$ catalyst. Further, the patentees present no examples employing such olefinic hydrocarbons.

We have now found that in isomerization with $TaF_5$ catalyst, heavy unbranched paraffins such as the straight-chain paraffins having about eight or more carbon atoms depress the production of desirable isomerization products such as isopentane, neohexane, cyclohexane and methylcyclohexane and we have further found that $C_8$–$C_{14}$ multiply-branches paraffins, for example, trimethylpentanes, promote the production of such isomerization products without appreciable alkylation.

The general object of this invention is to improve isomerization of feedstocks comprising saturated $C_5$ and $C_6$ hydrocarbons. Another object of this invention is to improve blending stock for motor fuel, such as gasoline, comprising isomerization products from light-naphtha streams comprising such saturated $C_5$ and $C_6$ hydrocarbons.

We have found that the objects of this invention can be obtained in an isomerization process which comprises isomerizing a hydrocarbon component comprising at least one saturated $C_5$–$C_6$ hydrocarbon in the presence of hydrogen and a catalyst comprising tantalum pentafluoride and hydrogen halide and in the presence of a hydrocarbon promoter comprising at least one member selected from the group consisting of $C_8$–$C_{14}$ multiply-branched paraffins, wherein the total concentration of $C_8$–$C_{14}$ multiply-branched paraffins is in the range of about 1 to 50 parts by weight per each 100 parts by weight of said saturated $C_5$–$C_6$ hydrocarbons.

Broadly, in the isomerization process of this invention, $C_8$–$C_{14}$ multiply-branched paraffins are employed to promote $TaF_5$/hydrogen halide catalyzed isomerization of $C_5$ saturated hydrocarbons, $C_6$ saturated hydrocarbons, and mixtures of such $C_5$–$C_6$ hydrocarbons, including pentanes, hexanes and methylcyclopentane, and to particularly promote production of isopentane and neohexane, which are high octane components for motor fuels such as gasoline.

The $C_5$–$C_6$ saturated hydrocarbons isomerized in the process of this invention can be obtained from the lighter components of typical petroleum naphtha. Light-naphtha isomerization feed in the process of this invention, having an end or maximum boiling point in the range of about 190° to 220° F. (88° to about 104° C.) containing components ranging from normal pentane with some normal heptane, can be obtained from a wide-boiling-range naphtha by separation as disclosed in our copending U.S. patent application Ser. No. 47,059, filed on even date herewith, in the names David A. McCaulay and Thomas D. Nevitt, titled *PROCESS FOR UPGRADING NAPHTHA HYDROCARBONS*, which is incorporated by reference herein. A preferred light-naphtha, boiling in the range of about 90°–210° F.

(32°–99° C.) comprises primarily pentanes, hexanes, heptanes, methylcyclopentane, cyclohexane and dimethylcyclopetanes.

In contrast to heavy straight-chain paraffins which interfere with $TaF_5$ catalyzed isomerization of $C_5$ and $C_6$ saturated hydrocarbons, under the same conditions, $C_8$–$C_{14}$ multiply branched paraffins appear to crack to form carbonium ions which promote isomerization of $C_5$ and $C_6$ saturated hydrocarbons, without appreciable alkylation.

As used herein, the term "$C_8$–$C_{14}$ multiply-branched paraffin" means acyclic paraffins having at least two alkyl branches and at least 8 to about 14 carbon atoms per molecule. Examples of such multiply-branched acyclic paraffins include, among others, isomers of trimethylpentanes, methyl ethyl pentanes, dimethyl hexanes, tetra metyl pentanes, dimethyl ethyl pentanes, trimethyl hexanes, methyl ethyl hexanes, dimethyl heptanes, pentamethyl pentane, trimethyl ethyl pentanes, methyl diethyl pentane, tetra methyl hexanes, dimethyl ethyl hexanes, diethyl hexanes, trimethyl heptanes, methyl ethyl heptanes, dimethyl octanes, penta methyl hexanes, trimethyl ethyl hexanes, methyl diethyl hexanes, tetra methyl heptanes, dimethyl ethyl heptanes, diethyl heptanes, methyl propyl heptanes, trimethyl octane, dimethyl nonane, hexa methyl hexanes, tetra methyl ethyl hexanes, dimethyl diethyl hexanes, pentamethyl heptanes, trimethyl methyl heptanes, methyl diethyl heptanes, dimethyl propyl heptanes, ethyl propyl heptanes, tetra methyl octanes, dimethyl ethyl octanes, diethyl octanes, methyl propyl octane, trimethyl nonane, methyl ethyl nonane, dimethyl decane, and similar materials having up to about 14 carbon atoms.

Such multiply-branched paraffins readily promote isomerization of $C_5$ and $C_6$ hydrocarbons with catalyst comprising $TaF_5$ and hydrogen halide, in contrast to the heavy straight chain and singly-branched paraffins of about 8 or more carbon atoms which appear to interfere with $C_5$ and $C_6$ isomerization. Cyclic paraffins do not readily crack nor appear to promote $C_5$ and $C_6$ isomerization. Generally, hydrocarbons having more than 14 carbon atoms are unsuitable for promotion of $C_5$ and $C_6$ isomerization in the process of this invention because of limited solubility of such heavy materials in the hydrogen halide isomerization reaction media.

Trimethylpentanes are the preferred multiply-branched paraffins employed as promoter in the process of this invention because of their superior reactivity in formation of carbonium ions and promotion of desirable $C_5$ and $C_6$ isomerization products. In the isomerization process, trimethylpentanes produce isobutane which does not alkylate and which can be recovered from the isomerization effluent and employed in separate production of alkylation products.

The $C_8$–$C_{14}$ multiply-branched paraffins employed in the process of this invention can be obtained from alkylation products, for example, products from typical refinery alkylation of butenes with isobutane to form trimethylpentane isomers and heavier isoparaffins. Heavy alkylate comprising $C_{12}$ multiply-branched hydrocarbons can be an economical source of isoparaffin promoter in the process of this invention.

The relative concentration of the $C_8$–$C_{14}$ multiply-branched paraffins charged in the isomerization process of this invention can be broadly within the range of about 1 to 50 parts by weight per each 100 parts by weight of saturated $C_5$–$C_6$ hydrocarbons in the isomerization feedstock. Suitable promotion of the desirable isomerization products can be obtained by employing a total concentration of $C_8$–$C_{14}$ multiply-branched paraffins in the range of about 2–30 parts by weight per 100 parts by weight of $C_5$–$C_6$ saturated hydrocarbons in the feedstock and best results determined by promotion of neohexane production in the isomerization product have been obtained in the range about 3–15 parts $C_8$–$C_{14}$ per 100 parts $C_5$–$C_6$ saturated hydrocarbons.

The light-naphtha isomerization feed can be treated to saturate or remove benzene in order to prevent benzene from deactivating the $TaF_5$ isomerization catalyst. Hydrotreatment of the light-naphtha under somewhat more severe conditions than conventional naphtha hydrofining-desulfurization can be employed in order to hydrogenate benzene as more fully disclosed in our aforesaid copending application Ser. No. 47,059. Alternatively, the light-naphtha isomerization feed can be treated to selectively adsorb benzene, for example, by contact with molecular sieve such as Linde 13X, manufactured by Union Carbide Corporation.

Isomerization of the light-naphtha fraction is carried out under hydrogen pressure to control cracking of the hydrocarbons, using a catalyst system comprising tantalum pentafluoride ($TaF_5$) in a protic acid solvent or diluent such as $HSO_3F$, perfluoroalkyl sulfonic acids, or hydrogen halide, preferably hydrogen fluoride, which is the preferred solvent because of its ease in separation from the isomerization products. Tantalum pentafluoride is meant to include tantalum pentafluoride as well as other fluoride species, e.g., ions such as $Ta_2F_{11}^-$, $Ta_3F_{16}$ and the like, that may be formed when tantalum pentafluoride is mixed with the hydrogen halide and the hydrocarbon reactants. Tantalum pentafluoride is also meant to include tantalum pentafluoride formed in situ as well as other species produced by the reaction of tantalum pentachloride or similar precursor with hydrogen fluoride. The diluent: $TaF_5$ weight ratio can range from about 50:1 to about 1:1 and preferably from about 6:1 to about 2:1 in order to maintain practical rate of reaction.

Reaction in the isomerization zone can be conducted as a batch or more preferably a continuous type of operation. In a preferred embodiment, hydrocarbon and catalyst are contacted and maintained substantially in the liquid forms with the reaction conducted in one or more reactors in concurrent, cross-current or counter-current flow typically employing conventional continuous stirred-tank reaction. In the isomerization reaction the presence of hydrogen minimizes heptane cracking and the formation of unsaturates which lead to the unsaturated "red-oil" which forms a complex deactivating the $TaF_5$ catalyst. However, high hydrogen pressures also slow down the overall rate of reaction so that the pressure must be adjusted to maintain balance between reaction rate and catalyst life. Suitably, hydrogen pressure of about 25 to about 1,000 psi (1.75 to about 70 kg/cm$^2$) can be employed with a temperature in the range of 0°–150° F. ($-18$°–66° C.). Preferably, hydrogen pressure in the isomerization zone can be about 100–800 psi (7–56 kg/cm$^2$) with temperature in the range of 70° to 125° F. (21° to 52° C.) and more preferably hydrogen pressure in the range of about 200–500 psi (14–35 kg/cm$^2$) is employed with a temperature in the range of about 70°–90° F. (21°–32° C.) to allow operation near ambient temperature.

Suitable space velocity in the isomerization zone can be within the range of about 0.5 to about 10 weight units of light-naphtha feed per hour per weight unit of $TaF_5$;

generally, lower temperature will require correspondingly lower space velocity and at ambient temperature in the range of about 70° to 125° F., (21° to 52° C.) space velocity should be between about 0.5 to about 5.0 WHSV, preferably about 0.5 to 2.5 WHSV.

Gradual deactivation of the TaF$_5$ catalyst caused by complex of the catalyst with polyunsaturated "red-oil" isomerization by-product will generally make necessary regeneration of the spent catalyst, preferably in a continuous catalyst regeneration zone. The spent catalyst can be regenerated by known methods such as treatment of the resinous by-product complex with hydrogen at elevated temperatures and pressures as disclosed in U.S. Pat. No. 4,120,912 (Hulme, 1978) or by displacement of TaF$_5$ from the resinous complex with a Lewis acid such as AlBr$_3$ as disclosed in U.S. Pat. No. 4,065,405 (Hulme, 1977), and both patents are incorporated herein by reference. Another method of regenerating the catalyst is hydrolysis of the by-product complex with sufficient water to separate the "red-oil" and subsequent dehydration of the hydrolyzed catalyst with molecular chlorine as disclosed in U.S. Pat. No. 4,069,268, (Siskin et al, 1978).

Isomerization of the light-naphtha produces conversion of methylcyclopentanes and dimethylcyclopentanes to the corresponding higher-boiling and equilibrium-favored cyclohexane and methylcyclohexane as well as isomerization of normal C$_5$-C$_7$ paraffins to branched paraffins having higher octane and C$_8$-C$_{14}$ multiply branched paraffins particularly promote the production of neohexane. As a result, isomerization of the light-naphtha produces substantial gain in the octane rating of the effluent. The effluent from the isomerization zone can be separated, suitably by distillation into an overhead fraction comprising primarily C$_5$ and C$_6$ branched paraffins and a heavier fraction comprising cyclohexane and methylcyclohexane naphthenes which can be dehydrogenated to aromatics, benzene and toluene, by conventional catalytic reforming.

Any suitable naphtha reforming process can be employed with the process of this invention such as typical commercial catalytic reforming processes, generally employing platinum-group metal catalysts, described in *Hydrocarbon Processing*, Vol. 57, No. 9, September, 1978, pp. 159–166, which is incorporated herein by reference. While a number of reactions take place during reforming, the primary reaction is the dehydrogenation of naphthenes to form aromatics.

In a preferred operation embodying the process of this invention, desulfurized and dearomatized light-naphtha can be pretreated with a stream of partially deactivated tantalum pentafluoride catalyst in solution of hydrogen fluoride taken from settling, in order to remove traces of aromatics, oxygen compounds and sulfur compounds that may be contained in the naphtha feed as disclosed in U.S. Pat. No. 4,058,575 which is incorporated herein by reference. The pretreated naphtha is next passed to the isomerization reactor to which a solution of TaF$_5$-HF catalyst solution in the ratio of about 0.1 to about 2.0 is continuously added with about 3-15 parts by weight C$_8$-C$_{14}$ multiply-branched paraffins per 100 parts C$_5$-C$_6$ saturated hydrocarbons in the light-naphtha. Hydrogen pressure of about 200-500 psi (14-35 Kg/cm$^2$) is maintained with a temperature of about 70° to 125° F. (21°-52° C.) in the isomerization reactor. Effluent from the isomerization reactor is sent to a settling vessel, where the catalyst and isomerization products separate into two liquid phases. The heavier catalyst phase is sent to catalyst regeneration and the hydrocarbon product is removed to a fractionator where isomerized paraffins are taken overhead and a naphthene-rich fraction is separately withdrawn.

The following examples are illustrative of this invention but do not indicate limitation upon the scope of the claims.

EXAMPLE 1

A straight-run, wide-boiling range naphtha, boiling in the range of from about 140° to about 350° F. (60° to about 175° C.) and containing about 248 ppm sulfur was analyzed and found to contain the following hydrocarbons:

| COMPONENT | | Wt. % |
|---|---|---|
| C6 | AROMATIC | 1.65 |
| C7 | AROMATIC | 3.22 |
| C8 | AROMATIC | 4.77 |
| C9 | AROMATIC | 0.736 |
| C6 | NAPHTHENE | 6.09 |
| C6 | PARAFFIN | 13.9 |
| C7 | NAPHTHENE | 11.6 |
| C7 | PARAFFIN | 18.5 |
| C8 | NAPHTHENE | 9.87 |
| C8 | PARAFFIN (Substantially normal and single branch) | 16.5 |
| C9 | NAPHTHENE | 4.31 |
| C9 | PARAFFIN (Substantially normal and single branch) | 7.77 |
| C10 | NAPHTHENE | 0.297 |
| C10 | PARAFFIN (Substantially normal and single branch) | 0.698 |

This wide-boiling range naphtha was fractionated in a bench-scale distillation column at a reflux ratio of about 4:1 to produce a light-naphtha overhead product in an amount of approximately 25 wt.% of the feed. The light-naphtha distillate fraction boiling in the range of about 90° to about 210° F. (32° to about 99° C.), and containing 195 ppm sulfur was analyzed to contain the following components:

| Component | WT. % |
|---|---|
| pentanes | 0.07 |
| 2,3-dimethylbutane | 0.27 |
| 2-methylpentane | 4.24 |
| 3-methylpentane | 6.52 |
| n-hexane | 31.26 |
| methylcyclopentane | 10.07 |
| dimethylpentanes | 5.61 |
| benzene | 5.21 |
| cyclohexane | 8.63 |
| 2-methylhexane | 7.70 |
| 3-methylhexane | 8.34 |
| dimethylcyclopentane | 8.65 |
| n-heptane | 2.58 |
| methylcyclohexane | 0.98 |

The bottom fraction, heavy-naphtha contained the balance of the feed components.

The light-naphtha distillate fraction was catalytically hydrotreated to remove sulfur and to dearomatize benzene and any traces of other aromatics in a fixed bed of approximately 30 cc of a 14-20 mesh (U.S. Sieve Series) commercial catalyst with the nominal composition 6 wt.% nickel oxide, 19 wt.% tungsten oxide, and 75 wt.% alumina oxide. The lined out hydrotreating reaction conditions include a temperature of about 660° F.

(349° C.), 850 psig (59.5 kg/cm$^2$) reactor pressure, hydrogen flow rate of about 2,000 SCF/bbl and a space velocity of about 0.67 weight units of hydrocarbon per hour per weight unit of catalyst. The hydrotreated light-naphtha was analyzed to contain the following components:

TABLE I

| Components in 210° F. end-boiling-point desulfurized, dearomatized light-naphtha | |
|---|---|
| Component | Wt.% |
| cyclopentane | 0.1 |
| 2,3-dimethylbutane | 0.6 |
| 2-methylpentane | 3.5 |
| 3-methylpentane | 5.6 |
| n-hexane | 29.6 |
| methylcyclopentane | 9.3 |
| dimethylpentanes | 6.1 |
| trimethylbutane | 0.1 |
| cyclohexane | 14.3 |
| methylhexanes | 19.8 |
| dimethylcyclopentanes | 8.2 |
| n-heptane | 2.0 |
| methylcyclohexane | 0.7 |
| benzene | <0.01 |
| toluene | <0.01 |

A continuous isomerization of the light-naphtha was carried out in a flow reaction system in which a 300 milliliter capacity reactor was equipped with a motor driven magnetic stirrer. Tantalum pentafluoride (20 g, 0.072 mole) was loaded into the reactor under nitrogen, the reactor was closed, and hydrogen fluoride (60 ml, 59.3 g, 2.96 mole) was metered in. Hydrogen flow and stirring (1,200 rpm) were started, and the hydrocarbon feed consisting of approximately 21 wt.% normal pentane and 79 wt.% light-naphtha having the component analysis presented in Table I was added rapidly at first to fill the reactor, and then a constant hydrocarbon feed flow rate was maintained at about 31 cc/hr corresponding to weight hourly space velocity of about 2 weight units of hydrocarbon feed per hour per weight unit of TaF$_5$. A low flow of hydrogen in contact with the vigorously stirred hydrocarbon-catalyst mixture maintained a pressure of about 1,000 psi (70 kg/cm$^2$) and the temperature was maintained at 85° F. (29° C.). Incoming feed continuously displaced hydrocarbon and a small amount of catalyst into a settling vessel where the catalyst was separated and returned to the reactor while the hydrocarbon product passed overhead into a product receiver in which the product hold up time was one hour or less. Product was periodically drawn from the product receiver and analyzed by gas chromatography with results at approximately 36 hours on stream presented as Run 1 in Table III. Results at 36 hours are indicative of average catalyst residence time which could be expected in an operation of the isomerization process with continuous catalyst regeneration.

EXAMPLE 2

Using the isomerization procedure, reactor and reaction conditions including the space velocity described in Example 1 isomerization was carried out upon a feed consisting of approximately 20 wt.% normal pentane, 75 wt.% light-naphtha having the component analysis presented in Table I, and 5 wt.% of a refinery alkylate having component analysis as follows:

TABLE II

| Major Components in Alkylate | |
|---|---|
| Component | Wt.% |
| trimethylpentanes | 63.0 |
| dimethylhexanes | 11.4 |
| trimethylhexanes | 8.1 |
| multiply-branched C$_{10}$ | 11.1 |
| multiply-branched C$_{11}$+ | 6.4 |

Results at approximately 36 hours on stream are presented as Run 2 in Table III.

EXAMPLE 3

Using the isomerization procedure, reactor and reaction conditions including the space velocity described in Example 1 isomerization was carried out upon a feed consisting of approximately 20 wt.% normal pentane, 70 wt.% light-naphtha presented in Table I and 10 wt.% of the alkylate presented in Table II. Results are presented as Run 3 in Table III, demonstrating that doubling the content of the alkylate in the feed in comparison to Example 2 did not significantly improve the isomerization product ratios.

EXAMPLE 4

Using the isomerization procedure, reactor and reaction conditions including the space velocity described in Example 1 isomerization was carried out on a feed consisting of approximately 10 wt.% normal pentane, 35 wt.% of the light-naphtha presented in Table I, 5 wt.% of the alkylate presented in Table II, and 50 wt.% normal nonane. Results demonstrating the detrimental influence of normal nonane in depressing the isomerization product ratios are presented as Run 4 in Table III.

EXAMPLE 5

The isomerization feed in Example 1 was isomerized using the same procedure, reactor and reaction conditions including space velocity as described therein with the exception that the hydrogen pressure was reduced to 250 psig and the temperature was maintained at 87° F. as shown in Run 5 in Table III with the results shown therein, indicating the improved isomerization products under the lower hydrogen pressure.

EXAMPLE 6

Using the isomerization procedure, reactor and reaction conditions including the space velocity described in Example 1 isomerization was carried out on a feed consisting of approximately 84.5 wt.% 3-methylpentane, 10.7 wt.% methylcyclopentane, and 4.8 wt.% isooctane (2,2,4-trimethylpentane). Results after 36 hours are presented as Run 6 in Table IV.

EXAMPLE 7

Example 6 was repeated with the addition to the feed of 2.3 wt.% benzene, demonstrating the severely impaired isomerization product ratios caused by benzene poisoning of the TaF$_5$ catalyst.

EXAMPLES 8-10

Using the isomerization procedure, reactor, and reaction conditions including the space velocity described in Example 1 isomerization was carried out on feeds presented in Table IV under Runs 8-10. Significantly, the substitution of normal nonane in the feed for Run 9 in comparison to the isooctane component in the feed for Run 8 demonstrates that the straight-chain heavier paraffins interfere with and depress the desired isomerization product ratios, and particularly depress the production of isopentane and neohexane.

TABLE III

| Run No. | 1 | 2 | 3 | 4 | 5 |
| --- | --- | --- | --- | --- | --- |
| Conditions | | | | | |
| Pressure, psig | 1,000 | 1,000 | 1,000 | 1,000 | 250 |
| Temperature, °F. | 85 | 85 | 85 | 85 | 87 |
| Catalyst | | | | | |
| TaF$_5$ g. | 20 | 20 | 20 | 20 | 20 |
| HF ml. | 60 | 60 | 60 | 60 | 60 |
| WHSV (g. feed/g. TaF$_5$) | 1.04 | 1.04 | 1.04 | 1.04 | 1.04 |
| Feed components, wt.% (selected) | | | | | |
| n-pentane | 19.6 | 19.2 | 20.6 | 11.2 | 18.8 |
| methylpentanes | 7.7 | 7.9 | 7.6 | 3.9 | 7.4 |
| n-hexane | 24.0 | 22.8 | 21.2 | 10.9 | 21.9 |
| methylcyclopentane (MCP) | 8.1 | 7.5 | 6.9 | 3.5 | 7.2 |
| cyclohexane | 11.1 | 10.6 | 9.7 | 5.1 | 10.5 |
| C$_8$+(alkylate) | — | 4.6 | 9.5 | 4.8 | 4.7 |
| dimethylcyclopentanes | 7.5 | 8.2 | 8.7 | 4.5 | 8.6 |
| methylcyclohexane (MCH) | 0.6 | 0.7 | 0.9 | 0.5 | 1.0 |
| n-nonane | | | | 49.0 | |
| Product components, wt.% (at 36 hours on stream) | | | | | |
| isobutane | 2.9 | 5.9 | 10.3 | 2.8 | 8.7 |
| neohexanes | 9.0 | 15.8 | 16.5 | 2.7 | 11.4 |
| C$_8$+(alkylate) | — | 0.6 | 0.4 | 1.7 | 0.8 |
| isopentanes | 5.2 | 12.7 | 14.4 | 0.2 | 14.4 |
| dimethylpentanes | 6.5 | 6.6 | 6.4 | 5.5 | 4.6 |
| methylcyclopentane (MCP) | 3.2 | 2.3 | 2.0 | 4.5 | 3.0 |
| cyclohexane | 14.8 | 12.7 | 9.5 | 7.3 | 14.4 |
| dimethylcyclopentanes | 0.6 | 0.6 | 0.7 | 0.6 | 4.3 |
| methylcyclohexane (MCH) | 7.5 | 7.6 | 7.2 | 1.9 | 8.5 |
| n-nonane | | | | 21.7 | |
| Product ratios | | | | | |
| isopentane/pentanes | .27 | .66 | .68 | .01 | .74 |
| neohexane/hexanes | .28 | .50 | .52 | .12 | .37 |
| cyclohexane/cyclohexane and MCP | .82 | .86 | .83 | .62 | .83 |
| methylcyclohexanes/MCH + DMCP's | .93 | .93 | .92 | .76 | .96 |

TABLE IV

| Run No. | 6 | 7 | 8 | 9 | 10 |
| --- | --- | --- | --- | --- | --- |
| Conditions | | | | | |
| Pressure, psi | 1,000 | 1,000 | 1,000 | 1,000 | 1,000 |
| Temperature, °F. | 75 | 75 | 85 | 85 | 85 |
| Catalyst | | | | | |
| TaF$_5$ g. | 10 | 10 | 20 | 20 | 20 |
| HF ml. | 60 | 60 | 60 | 60 | 60 |
| WHSV | 2.06 | 2.16 | 1.10 | 1.05 | 1.04 |
| Feed components, wt.% | | | | | |
| 3-methylpentane | 84.5 | 82.8 | 75.0 | 68.3 | 2.5 |
| n-hexane | | | | | 72.9 |
| methylcyclopentane (MCP) | 10.7 | 10.0 | 20.0 | 22.4 | 19.2 |
| isooctane | 4.8 | 4.8 | 5.0 | — | 5.4 |
| benzene | | 2.3 | | | |
| n-nonane | | | | | 9.4 |
| Product components, wt.% (at 36 hours on stream) | | | | | |
| isobutane | 3.9 | 3.3 | 5.4 | 0.2 | 4.2 |
| neohexane | 8.3 | 1.6 | 18.9 | 3.4 | 27.2 |
| isooctane | 0.5 | 1.1 | 0.2 | — | 1.9 |
| methylcyclopentane (MCP) | 1.4 | 4.6 | 2.3 | 4.2 | 1.1 |
| cyclohexane (CH) | 9.2 | 4.9 | 17.5 | 16.9 | 12.0 |
| benzene | | 1.7 | | | |
| n-nonane | | | | | 1.3 |
| Product ratios | | | | | |
| cyclohexane / MCP + CH | .86 | .52 | .88 | .80 | .92 |
| neohexane / total hexanes | .097 | .019 | .26 | .049 | .36 |

We claim:

1. An isomerization process which comprises isomerizing a hydrocarbon stream comprising at least one saturated C$_5$–C$_6$ hydrocarbon in the presence of hydrogen and a catalyst comprising tantalum pentafluoride and hydrogen halide and in the presence of a hydrocarbon promoter comprising at least one member selected from the group consisting of C$_8$–C$_{14}$ multiple-branched paraffins, wherein the total concentration of C$_8$–C$_{14}$ multiple-branched paraffins is in the range of about 1 to 50 parts by weight per 100 parts by weight of said saturated C$_5$–C$_6$ hydrocarbons.

2. The process of claim 1 wherein said hydrocarbon promoter comprises trimethylpentane.

3. The process of claim 1 wherein said hydrocarbon promoter consists essentially of one member selected from the group consisting of C$_8$–C$_{14}$ multiple-branched paraffins.

4. The process of claim 1 wherein said hydrocarbon promoter consists essentially of isoalkane/olefin alkylation product.

5. The process of claim 1 wherein the total concentration of C$_8$–C$_{14}$ multiple-branched paraffins is in the range of about 3–15 parts by weight per 100 parts by weight of said saturated C$_5$–C$_6$ hydrocarbons.

6. The process of claim 1 wherein said hydrocarbon stream consists essentially of said C$_5$ and C$_6$ saturated hydrocarbons.

7. The process of claim 1 wherein said hydrogen halide comprises hydrogen fluoride.

8. The process of claim 1 wherein said isomerization is carried out under hydrogen partial pressure in the range of about 25–1000 psi (1.75–70 kg/cm$^2$), at a temperature in the range of about 0°–150° F. (−17° to 66° C.).

9. The process of claim 1 wherein said isomerization is carried out under hydrogen partial pressure in the range of about 200–500 psi (14–35 kg/cm$^2$), at a temperature in the range of about 70°–90° F. (21°–32° C.).

* * * * *

UNITED STATES PATENT OFFICE
CERTIFICATE OF CORRECTION

Patent No. 4,214,116              Dated July 22, 1980

Inventor(s) David A. McCaulay and Thomas D. Nevitt

It is certified that error appears in the above-identified patent and that said Letters Patent are hereby corrected as shown below:

| Patent Column | Line | |
|---|---|---|
| 1 | 61 | "Particularly" should be --preferably--. |
| 2 | 22 | "multiply-branches" should be --multiply-branched. |
| 3 | 17 | "tetra metyl pentanes" should be --tetra methyl pentanes--. |
| 10 | 9 | "9.2  4.9  17.5  16.9  12.0" should be -- 9.1  4.9  17.5  16.9  12.0--. |

Signed and Sealed this

Twenty-fourth Day of February 1981

[SEAL]

Attest:

RENE D. TEGTMEYER

Attesting Officer   Acting Commissioner of Patents and Trademarks